United States Patent [19]

Reising

[11] Patent Number: 4,988,345

[45] Date of Patent: Jan. 29, 1991

[54] ABSORBENT ARTICLES WITH RAPID ACQUIRING ABSORBENT CORES

[75] Inventor: George S. Reising, Batavia, Ohio

[73] Assignee: The Procter & Gamble Company, Cincinnati, Ohio

[21] Appl. No.: 198,036

[22] Filed: May 24, 1988

[51] Int. Cl.⁵ .............................................. A61F 13/16
[52] U.S. Cl. ..................................... 604/368; 604/378
[58] Field of Search ................... 604/368, 378, 385.1, 604/385.2

[56] References Cited

U.S. PATENT DOCUMENTS

| | | | |
|---|---|---|---|
| 810,120 | 1/1906 | Green | 604/378 |
| 2,043,325 | 6/1936 | Jackson, Jr. | 604/378 |
| 3,029,817 | 4/1962 | Harwood et al. | 604/372 |
| 3,046,986 | 7/1962 | Harwood | 604/378 |
| 3,371,667 | 3/1968 | Morse | 604/369 |
| 3,441,023 | 4/1969 | Rijssenbeck | 604/378 |
| 3,441,024 | 4/1969 | Ralph | 604/398 |
| 3,491,759 | 1/1970 | Samuel | 604/378 |
| 3,593,716 | 7/1971 | Vogt | 604/366 |
| 3,593,717 | 7/1971 | Jones, Sr. | 604/378 |
| 3,620,894 | 11/1971 | Osten | 428/139 |
| 3,665,920 | 5/1972 | Davis | 604/377 |
| 3,759,262 | 9/1973 | Jones, Sr. | 604/378 |
| 3,844,288 | 10/1974 | Kiela | 604/379 |
| 3,889,679 | 6/1975 | Taylor | 604/378 |
| 3,934,588 | 1/1976 | Mesek et al. | 604/378 |
| 3,987,792 | 10/1976 | Hernandez et al. | 604/365 |
| 4,027,672 | 6/1977 | Karami | 604/385.1 |
| 4,173,046 | 11/1979 | Gallagher | 604/378 |
| 4,285,342 | 8/1981 | Mesek | 604/375 |
| 4,289,130 | 9/1981 | Usami et al. | 604/372 |
| 4,381,782 | 5/1983 | Mazurak et al. | 604/368 |
| 4,397,644 | 8/1983 | Matthews et al. | 604/378 |
| 4,410,324 | 10/1983 | Sabee | 604/385.2 |
| 4,413,996 | 11/1983 | Taylor | 604/382 |
| 4,480,000 | 10/1984 | Watanabe et al. | 604/370 |
| 4,501,586 | 2/1985 | Holtman | 604/385.1 |
| 4,505,705 | 3/1985 | Matthews et al. | 604/385.1 |
| 4,518,451 | 5/1985 | Luceri et al. | 604/378 |
| 4,531,945 | 7/1985 | Allison | 604/378 |
| 4,540,454 | 9/1985 | Pieniak et al. | 604/378 |
| 4,551,143 | 11/1985 | Cook et al. | 604/371 |
| 4,560,372 | 12/1985 | Pieniak | 604/368 |
| 4,610,678 | 9/1986 | Weisman et al. | 604/368 |
| 4,623,340 | 11/1986 | Luceri | 604/385.1 |
| 4,673,402 | 6/1987 | Weisman et al. | 604/368 |
| 4,676,784 | 6/1987 | Erdman et al. | 604/368 |
| 4,676,786 | 6/1987 | Nishino | 604/378 |
| 4,678,464 | 7/1987 | Holtman | 604/385.1 |
| 4,704,112 | 11/1987 | Suzuki et al. | 604/378 |
| 4,731,065 | 3/1988 | Yamada | 604/378 |
| 4,731,071 | 3/1988 | Pigneul | 604/368 |
| 4,738,676 | 4/1988 | Osborn, III | 604/378 |
| 4,781,962 | 11/1988 | Zamarripa et al. | 604/378 |

FOREIGN PATENT DOCUMENTS

| | | |
|---|---|---|
| 0062495A2 | 10/1982 | European Pat. Off. . |
| 0944242 | 6/1956 | Fed. Rep. of Germany ... 604/385.1 |
| 0389368 | 3/1933 | United Kingdom ................ 604/378 |
| 2124907A | 2/1984 | United Kingdom . |

Primary Examiner—Stephen O. Pellegrino
Assistant Examiner—Sharon Rose
Attorney, Agent, or Firm—Jeffrey V. Bamber; Steven W. Miller; Richard C. Witte

[57] ABSTRACT

Absorbent articles such as disposable diapers, incontinent pads, sanitary napkins and the like that have absorbent cores that are suitable for rapidly acquiring and containing liquid in an especially effective and efficient manner. The absorbent core comprises a storage layer comprising hydrophilic fibrous material and discrete particles of absorbent gelling material and having an acquisition aperture so it can quickly acquire this discharged liquid; and a liquid handling layer comprising a resilient material that is moisture insensitive so to rapidly acquire liquids into itself through the acquisition aperture and distribute the liquid throughout the liquid handling layer to the storage layer. The storage layer also allows the liquid handling layer to be "drained" of the liquid that is acquired so that the liquid handling layer may have sufficient capacity to acquire and distribute subsequent loading of liquids.

25 Claims, 2 Drawing Sheets

ABSORBENT ARTICLES WITH RAPID ACQUIRING ABSORBENT CORES

FIELD OF THE INVENTION

This invention relates to absorbent articles, such as disposable diapers, adult incontinent pads, sanitary napkins and the like. More particularly, the invention relates to absorbent cores for such absorbent articles for quickly acquiring and distributing liquids to the storage layer.

BACKGROUND OF THE INVENTION

Absorbent articles such as disposable diapers, adult incontinent pads, sanitary napkins and the like are generally provided with an absorbent core to receive and retain body liquids. In order for such absorbent articles to function efficiently, the absorbent core must quickly acquire body liquids into the structure from the point of application and subsequently distribute the body liquids within and throughout the absorbent core to provide maximum leakage containment. In addition, the absorbent core should be capable of retaining the absorbed liquids when placed under load and have a renewable liquid capacity for acquiring subsequent voids of liquids.

Previous attempts to improve the effectiveness of absorbent cores have included distributing particles of absorbent gelling material throughout or in portions of the absorbent core. For example, U.S. Pat. No. 4,610,678 issued to Paul T. Weisman and Stephen A. Goldman on Sept. 9, 1986, discloses absorbent members wherein particles of absorbent gelling material (hydrogel) are dispersed in an air-laid web of hydrophilic fibrous material and compressed to a particular density. U.S. Pat. No. 4,673,402 issued to Paul T. Weisman, Dawn I. Houghton, and Dale A. Gellert on June 16, 1987, discloses a dual-layer absorbent core wherein an absorbent acquisition/distribution layer overlays a lower fluid storage layer that consists essentially of a uniform combination of hydrophilic fibrous material and discrete particles of absorbent gelling material (hydrogel). European Pat. Application No. EP-A-254,476; The Procter & Gamble Company; published Jan. 27, 1988, discloses absorbent members having a storage zone and an acquisition zone having a lower average density and a lower average basis weight per unit area than the storage zone so that the acquisition zone may effectively and efficiently acquire discharged liquid.

It has been found that the effectiveness of absorbent gelling material in disposable absorbent articles is quite dependent upon the form, position, and/or manner in which the particles of absorbent gelling material are incorporated into the absorbent core. In some cases, for example, the effectiveness of absorbent cores containing particles of absorbent gelling material can be adversely affected by a phenomenon called gel blocking. The term gel blocking describes a situation that occurs when a particle of absorbent gelling material is wetted, the surface of the particle swelling so as to inhibit liquid transmission into the interior of the absorbent core. Wetting of the interior absorbent core, therefore, takes place via very slow diffusion process. In practical terms, this means that acquisition of liquid by the absorbent core is much slower than the discharge of the liquids to be absorbed, and leakage from the absorbent article may take place well before the particles of absorbent gelling material in the absorbent core are fully saturated or before the liquid can diffuse or wick past the "blocking" particles into the rest of the absorbent core. The slow acquisition rate also fails to take advantage of the rapid wicking of liquids to other parts of the absorbent core provided by a densified absorbent core containing particles of absorbent gelling material.

The structure of the absorbent core may also contribute to leakage of liquids by not providing sufficient capacity for quantities of liquids deposited onto the absorbent core after the initial gush of liquid has been deposited onto the absorbent core. Gel blocking and saturation of the materials adjacent the zone of application inhibit acquisition and transmission of these liquids into and throughout the core such that the absorbent core has no additional capacity to absorb these liquids so that there is an increased likelihood of such liquids leaking out of the edges of the absorbent article. Thus, efficient and rapid acquisition and distribution of liquids by and from the initial layers of the core is necessary to insure sufficient capacity for subsequently deposited liquids.

Thus, it would be advantageous to provide an absorbent core that quickly acquires and distributes large quantities of liquids within itself while minimizing gel blocking during the liquid acquisition stage and providing a renewable liquid capacity for acquiring subsequent voids of liquids. It is, therefore, a primary objective of the present invention to provide absorbent cores which are especially effective and efficient in their use of absorbent gelling materials and acquisition/distribution materials.

SUMMARY OF THE INVENTION

The present invention provides absorbent articles such as disposable diapers, incontinent pads, sanitary napkins and the like that have absorbent cores that are suitable for rapidly acquiring and containing liquids in an especially effective and efficient manner. Such absorbent articles comprise a liquid pervious topsheet, a liquid impervious backsheet joined with the topsheet, and an absorbent core positioned between the topsheet and the backsheet.

The absorbent core comprises at least two layers including a storage layer comprising a combination of hydrophilic fibrous material and discrete particles of absorbent gelling material, and a liquid handling layer comprising a resilient, low density, high void volume material that is moisture insensitive so as to rapidly acquire into itself liquids and distribute the liquids throughout the liquid handling layer to remote portions of the storage layer. The storage layer is provided with an acquisition aperture to allow liquids to pass through the storage layer and onto the liquid handling layer. The storage layer contains and stores the liquids deposited onto the absorbent core by allowing the liquid handling layer to be "drained" of the liquids it rapidly acquires so that the liquid handling layer may have sufficient capacity to acquire and distribute subsequent loadings of liquids.

The present invention also relates to absorbent cores, per se, of the type heretofore described, which can be employed in absorbent articles. Cores of the type utilized herein in absorbent articles, in addition to providing especially efficient and effective use of absorbent gelling materials, are also especially effective in acquiring, distributing, and storing subsequent loadings of liquids.

BRIEF DESCRIPTION OF THE DRAWINGS

While the specification concludes with claims which particularly point out and distinctly claim the subject matter regarded as forming the present invention, it is believed that the invention will be better understood from the following description taken in conjunction with the accompanying drawings in which:

DETAILED DESCRIPTION OF THE INVENTION

Figure 1:
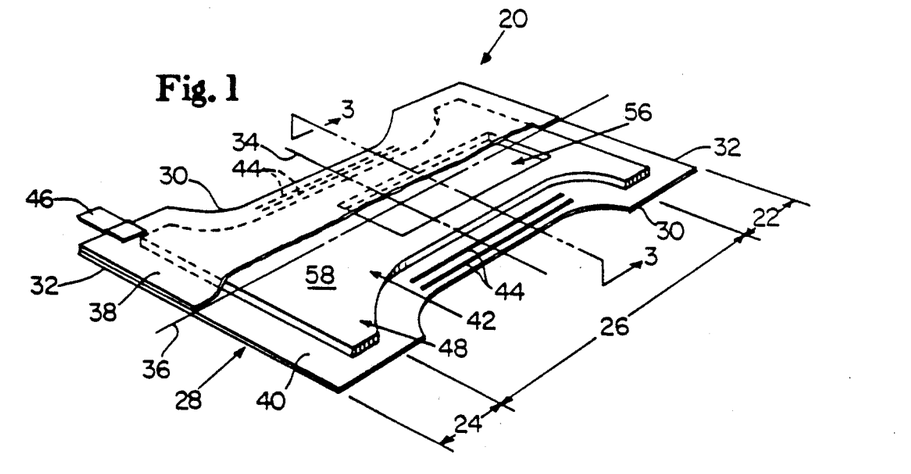
FIG. 1 is a perspective view of a disposable diaper embodiment of the present invention wherein portions of the topsheet and top tissue layer have been cut-away so as to more clearly show the underlying absorbent core of the diaper.

The absorbent cores of the present invention will be described herein in relationship to their use in disposable absorbent articles; however, it should be understood that the potential application of the absorbent cores of the present invention should not be limited to disposable absorbent articles. As used herein, the term "disposable absorbent article" refers to articles which absorb and contain body exudates and, more specifically, refers to articles which are placed against or in proximity to the body of the wearer to absorb and contain the various exudates discharged from the body, and which are intended to be discarded after a single use (i.e., they are not intended to be laundered or otherwise restored or reused). A preferred embodiment of a disposable absorbent article, diaper 20, is shown in FIG. 1. As used herein, the term "diaper" refers to a garment generally worn by infants and incontinent persons that is worn about the lower torso of the wearer. It should be understood, however, that the present invention is also applicable to other disposable absorbent articles such as incontinent briefs, incontinent pads, sanitary napkins and the like.

FIG. 1 is a perspective view of the diaper 20 of the present invention with portions of the structure being cut-away to more clearly show the construction of the diaper 20. The diaper is shown in FIG. 1 to have a front region 22, a back region 24, a crotch region 26, and a periphery 28 which is defined by the outer edges of the diaper in which the longitudinal edges are designated 30 and the end edges are designated 32. The diaper additionally has a transverse centerline 34 and a longitudinal centerline 36.

The diaper 20 comprises a liquid pervious topsheet 38; a liquid impervious backsheet 40; an absorbent core 42; elastic members 44; and tape tab fasteners 46 (only one being shown in FIG. 1). While the topsheet 38, the backsheet 40, the absorbent core 42, and the elastic members 44 may be assembled in a variety of well-known configurations, a preferred diaper configuration is described generally in U.S. Pat. No. 3,860,003 entitled "Contractable Side Portions For Disposable Diaper", which issued to Kenneth B. Buell on Jan. 14, 1975, and which patent is incorporated herein by reference.

FIG. 1 shows a preferred embodiment of the diaper 20 in which the topsheet 38 and the backsheet 40 are co-extensive and have length and width dimensions generally larger than those of the absorbent core 42. The topsheet 38 is joined with and superimposed on the backsheet 40 thereby preferably forming the periphery 28 of the diaper 20. The periphery 28 defines the outer perimeter or the edges of the diaper 20. The periphery 28 comprises the longitudinal edges 30 and the end edges 32.

The diaper 20 has front and back regions 22 and 24, respectively, extending from the end edge 32 of the diaper periphery 28 toward the transverse centerline 34 of the diaper 20 a distance from about 2% to about 20%, preferably about 10%, of the length of the diaper. The front and back regions comprise those portions of the diaper 20, which when worn, encircle the waist of the wearer. The crotch region 26 is that portion of the diaper 20 between the front region 22 and the back region 24, and comprises that portion of the diaper 20 which, when worn, is positioned between the legs of the wearer. Thus, the crotch region 26 defines the area of typical liquid deposition for a diaper 20 or other disposable absorbent articles.

Figure 2:
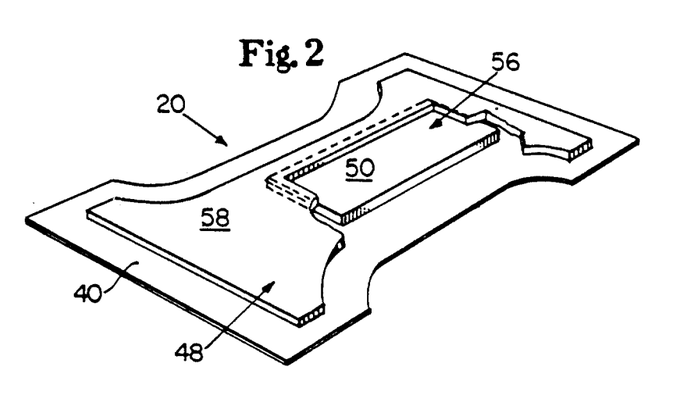
FIG. 2 is a perspective view of the disposable diaper of the present invention wherein the topsheet and top tissue layer have been removed and the storage layer of the absorbent core has been cut-away to more clearly show the underlying liquid handling layer of the absorbent core.

FIG. 2 shows the preferred embodiment of the diaper 20 of the present invention, with portions of the diaper 20 removed, so as to more clearly show the absorbent core 42 of the present invention. The absorbent core 42 preferably comprises a storage layer 48 and a liquid handling layer 50. The storage layer 48 has a generally hourglass-shape and an acquisition aperture 56 preferably the rectangular acquisition aperture as shown in FIG. 2, and a holding zone 58 that at least partially laterally surrounds the perimeter of the acquisition aperture 56. The liquid handling layer 50 is the generally rectangular layer positioned subjacent at least the acquisition aperture 56.

Figure 3:
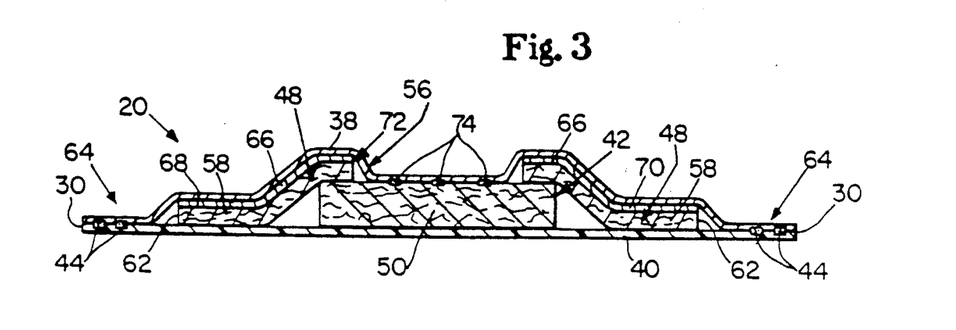
FIG. 3 is a transverse sectional view of the disposable diaper of the present invention taken along section line 3—3 of FIG. 1.

FIG. 3 is a cross-sectional view taken along line 3—3 of FIG. 1 that depicts the diaper construction in the area of typical liquid deposition. The absorbent core 42 comprises the storage layer 48 having an acquisition aperture 56 and a holding zone 58, and a liquid handling layer 50 positioned subjacent the storage layer 48 so as to be positioned between the storage layer 48 and the backsheet 40. The storage layer 48 comprises a combination of hydrophilic fibrous material and discrete particles of absorbent gelling material. The absorbent core 42 is positioned between the topsheet 38 and the backsheet 40, both the topsheet 38 and the backsheet 40 preferably extending beyond the side edges 62 of the absorbent core 42 to define side flaps 64. The topsheet 38 and the backsheet 40 also enclose the elastic members 44 adjacent the longitudinal edge 30 in the side flaps 64. A top tissue layer 66 is disposed between the topsheet 38 and the storage layer 48 of the absorbent core 42 so as to provide integrity for the storage layer 48 during processing and handling of the absorbent core 42. The top tissue layer 66 preferably comprises a first tissue layer 68 and a second tissue layer 70 laterally spaced from each other to provide a tissue acquisition aperture 72 that generally corresponds to the acquisition aperture 56 positioned in the storage layer 48 so that liquids deposited onto the topsheet 38 will quickly be acquired into the liquid handling layer 50. The topsheet 38 is also preferably directly joined to the liquid handling layer 50 through the acquisition aperture 56 of the storage layer 48 and the tissue acquisition aperture 72 of the top tissue layer 66 by attachment means 74. Since the topsheet 38 is joined directly to the liquid handling layer 50 through the acquisition aperture 56, liquids tend to more quickly pass through the topsheet 38 to the liquid handling layer 50 and have a reduced tendency to pool on the topsheet 38.

The topsheet 38 is compliant, soft feeling, and non-irritating to the wearer's skin. Further, the topsheet 38 is liquid pervious permitting liquids to readily penetrate through its thickness. A suitable topsheet 38 may be manufactured from a wide range of materials, such as porous foams, reticulated foams, apertured plastic films, natural fibers (e.g., wood or cotton fibers), synthetic fibers (e.g., polyester or polypropylene fibers) or from a combination of natural and/or synthetic fibers. Preferably, the topsheet 38 is made of a hydrophobic material to isolate the wearer's skin from liquids in the absorbent core 42.

A particularly preferred topsheet 38 comprises staple length polypropylene fibers having a denier of about 1.5, such as Hercules Type 151 polypropylene marketed by Hercules, Inc. of Wilmington, Del. As used herein, the term "staple length fibers" refers to those fibers having a length of about 15.9 mm (0.62 inches).

There are a number of manufacturing techniques which may be used to manufacture the topsheet 38. For example, the topsheet 38 may be woven, non-woven, spunbonded, carded or the like. A preferred topsheet is carded and thermally bonded by means well-known to those skilled in the fabric art. Preferably, the topsheet 38 has a weight from about 18 to about 25 grams per square meter, a minimum dry tensile strength of at least about 400 grams per centimeter in the machine direction and a wet tensile strength of at least about 55 grams per centimeter in the cross-machine direction The backsheet 40 is impervious to liquids and is preferably manufactured from a thin plastic film, although other selectable liquid impervious materials may also be used. The backsheet 40 prevents the exudates absorbed and contained in the absorbent core 42 from wetting articles which contact the diaper 20 such as bedsheets and undergarments. Preferably, the backsheet 40 is a polyethylene film having a thickness of from about 0.012 mm (0.5 mil) to about 0.051 cm (2.0 mils), although other flexible, liquid impervious materials may be used. As used herein, the term "flexible" refers to materials which are compliant and which readily conform to the general shape and contours of the wearer's body.

A suitable polyethylene film is manufactured by Monsanto Chemical Corporation and marketed in the trade as Film No. 8020. The backsheet 40 is preferably embossed and/or matte finished to provide a more clothlike appearance. Further, the backsheet 40 may permit vapors to escape from the absorbent core 42 while still preventing exudates from passing through the backsheet 40.

The size of the backsheet 40 is dictated by the size of the absorbent core 42 and the exact diaper design selected. In a preferred embodiment, the backsheet 40 has a modified hourglass-shape extending beyond the absorbent core 42 a minimum distance of at least about 1.3 cm to about 2.5 cm (about 0.5 to about 1.0 inch) around the entire diaper periphery 28.

The topsheet 38 and the backsheet 40 are joined to each other in any suitable manner. As used herein, the term "joined" encompasses configurations whereby the topsheet 38 is directly secured to the backsheet 40 by affixing the topsheet 38 directly to the backsheet 40, and configurations whereby the topsheet 38 is indirectly secured to the backsheet 40 by affixing the topsheet 38 to intermediate members which in turn are affixed to the backsheet 40. In a preferred embodiment, the topsheet 38 and the backsheet 40 are joined directly to each other in the diaper periphery 28 by attachment means (not shown) such as an adhesive or any other attachment means as known in the art. For example, a uniform continuous layer of adhesive, a patterned layer of adhesive, or an array of separate lines or spots of adhesive may be used to join the topsheet 38 to the backsheet 40.

Tape tab fasteners 46 are typically applied to the back region 24 of the diaper 20 to provide a fastening means for holding the diaper on the wearer. Only one of the tape tab fasteners is shown in FIG. 1. The tape tab fasteners 46 can be any of those well known in the art, such as the fastening tapes disclosed in U.S. Pat. No. 3,848,594 entitled "Tape Fastening System For Disposable Diaper" which issued to Kenneth B. Buell on Nov. 19, 1974, and which patent is incorporated herein by reference. These tape tab fasteners 46 or other diaper fastening means, such as pins, "Velcro" type mechanical fasteners or other fasteners, are typically applied near the corners of the diaper 20.

The elastic members 44 are disposed adjacent the periphery 28 of the diaper 20, preferably along each longitudinal edge 30, so that the elastic members 44 tend to draw and hold the diaper 20 against the legs of the wearer to form leg cuffs. Alternatively, or in addition, elastic members may be disposed adjacent either or both of the end edges 32 of the diaper 20 to provide a waistband. (For example, a suitable waistband is disclosed in U.S. Pat. No. 4,515,595 entitled "Disposable Diapers With Elastically Contractible Waistband", which issued to David J. Kievit and Thomas F. Osterhage on May 7, 1985, and which patent is incorporated herein by reference.) In addition, a method and apparatus suitable for manufacturing a disposable diaper having elastically contractible elastic members is described in U.S. Pat. No. 4,081,301 entitled "Method And Apparatus For Continuously Attaching Discrete, Stretched Elastic Strands To Predetermined Isolated Portions Of Disposable Absorbent Products" which issued to Kenneth B. Buell on Mar. 28, 1978, and which patent is incorporated herein by reference.

The elastic members 44 are secured to the diaper 20 in an elastically contractible condition so that in a normally unrestrained configuration, the elastic members 44 effectively contract or gather the diaper 20. The elastic members 44 can be secured in an elastically contractible condition in at least two ways. For example, the elastic members 44 may be stretched and secured while the diaper 20 is in an uncontracted condition. Alternatively, the diaper 20 may be contracted, for example, by pleating, and the elastic members 44 secured and connected to the diaper 20 while the elastic members 44 are in their unrelaxed or unstretched condition.

In the embodiment illustrated in FIG. 1, the elastic members 44 extend essentially the entire length of the diaper 20 in the crotch region 26. Alternatively, the elastic members 44 may extend the entire length of the diaper 20, or any other length suitable to provide elastically contractible lines. The length of the elastic members 44 is dictated by the diaper's design.

The elastic members 44 may take a multitude of configurations. For example, the width of the elastic members 44 may be varied from about 0.25 mm (0.01 inches) to about 25 mm (1.0 inch) or more; the elastic members 44 may comprise a single strand of elastic material or may comprise several parallel or non-parallel strands of elastic material; or the elastic members 44 may be rectilinear or curviliner. Still further, the elastic members 44 may be affixed to the diaper in any of several ways which are well-known in the art. For example, the elastic members 44 may be ultrasonically bonded, heat and pressure sealed into the diaper 20 using a variety of bonding patterns, or the elastic members 44 may simply be adhesively secured (e.g., glued) to the diaper 20. An elastic member which has been found to be suitable for use in such a diaper is an elastic strand made from natural rubber such as elastic tape sold under the tradename Fulflex 9211 by Fulflex Company of Scotland, N.C.. Other suitable elastic members may comprise a wide variety of materials as are well known in the art including elastomeric films, polyurethane films, elastomeric foams, formed elastic scrim, and heat shrinkable elastic material.

The absorbent core 42, which is preferably flexible, is positioned between the topsheet 38 and the backsheet 40 to form the diaper 20. The absorbent core 42 is generally compressible, conformable, non-irritating to the wearer's skin, and capable of absorbing and retaining liquids and certain body exudates. The absorbent core 42 essentially comprises a storage layer 48 and a liquid handling layer 50. It should be understood that for purposes of this invention, these types of layers refer merely to zones of the absorbent core and are not necessarily limited to single layers or sheets of material. Thus, the storage layer 48 and the liquid handling layer 50 may actually comprise laminates or combinations of several sheets or webs of the requisite type of materials as hereinafter described. Thus, as used herein, the term "layer" includes the term "layers" and "layered".

The storage layer 48 of the absorbent core 42 of the diaper 20 herein preferably comprises a combination of hydrophilic fibrous material and discrete particles of absorbent gelling material. The storage layer 48 serves to collect and hold discharged body liquids deposited onto the storage layer 48 or distributed to the storage layer 48 by the liquid handling layer 50, to retain such liquid under the pressures encountered as a result of the wearer's movement, to prevent already acquired liquids from passing out of the core back through the topsheet 38 and onto the skin of the wearer, and to provide a secondary gush capacity for the absorbent core 42. Ideally, the storage layer 48 will drain the liquid handling layer 50 of much of its acquired liquid load. The storage layer 48 comprises an acquisition aperture 56 and a holding zone 58 in liquid communication with at least a lateral portion of the acquisition aperture 56. The holding zone 58 generally comprises the remainder of the storage layer 48.

Various types of hydrophilic material can be used in the storage layer 48 of the absorbent core 42. Any type of hydrophilic fibers which are suitable for use in conventional absorbent products are also suitable for use in the storage layer 48 of the absorbent core 42 of the present invention. Specific examples of preferred hydrophilic fibers include cellulose fibers, rayon, and polyester fibers. Other examples of suitable hydrophilic fibers are hydrophilized hydrophobic fibers, such as surfactant-treated or silica-treated thermoplastic fibers. For reasons of availability and cost, cellulose fibers, in particular, wood pulp fibers are preferred.

Suitable absorbent gelling materials can be inorganic materials such as silica gels or organic compounds such as cross-linked polymers. Cross-linking may be by covalent, ionic, van der Walls, or hydrogen bonding. Examples of absorbent gelling material polymers include polyacrylamides, polyvinyl alcohol, ethylene-maleic anhydride copolymers, polyvinyl ethers, hydroxypropyl cellulose, carboxymethyl cellulose, polyvinyl morpholine, polymers and copolymers of vinyl sulfonic acid, polyacrylates, polyacrylamides, polyvinyl paradene and the like. Other suitable hydrogels are disclosed in U.S. Pat. No. 3,901,236 entitled "Disposable Absorbent Articles Containing Hydrogel Composites Having Improved Fluid Absorption Efficiencies And Processes For Preparation", issued to Assaron et al on Aug. 26, 1975, and in U.S. Pat. Re. No. 32,649 entitled "Hydrogel-Forming Polymer Compositions For Use In Absorbent Structures", which issued to Kerryn A. Brandt, Stephen A. Goldman and Thomas A. Inglin on Apr. 19, 1988, both of which are incorporated herein by reference. Particularly preferred polymers for use in the absorbent core include hydrolized acrylonitrile grafted starch, acrylic acid grafted starch, polyacrylate and maleic anhydride copolymers, or mixtures thereof.

The relative amount of hydrophilic fibrous material and particles of absorbent gelling material used in the storage layer 48 can be most conveniently expressed in terms of a weight percentage of the storage layer 48. The storage layer 48 preferably contains from about 2% to about 60%, more preferably from about 9% to about 50%, and most preferably from about 10% to about 25%, by weight, of the storage layer 48 of particles of absorbent gelling material. This concentration of absorbent gelling material can also be expressed in terms of a weight ratio of fiber to particulate. These ratios may range from about 40:60 to about 98:2 or from about 75:25 to about 90:10. For most commercially available absorbent gelling materials, the optimum fiber-to-particulate weight ratio is in the range of from about 50:50 to about 91:9.

In addition, the particles of absorbent gelling material may be dispersed in various ratios throughout different regions and thicknesses of the storage layer 48. For example, the combination of hydrophilic fibrous material and particles of absorbent gelling material may be disposed only in certain portions of the storage layer 48. The storage layer 48 preferably contains an intimate admixture of hydrophilic fibrous material and discrete particles of absorbent gelling material. It is most preferred that the particles are substantially uniformly distributed throughout the entire storage layer 48.

Alternatively, the storage layer 48 can comprise a laminate or particles of absorbent gelling material overwrapped with webs of fibrous material such as tissue paper. Such a laminate of structure is more fully described in U.S. Pat. No. 4,578,068 entitled "Absorbent Laminate Structure", which issued to Timothy A. Kramer, Gerald A. Young, and Ronald W. Kock on Mar. 25, 1986, which patent is incorporated herein by reference.

The size, shape, and character, including capillarity (e.g., pore size or density and basis weight) of the storage layer 48 has some importance in determining the effectiveness of the resulting absorbent cores in absorbing discharged body liquids. As shown in FIG. 1, the storage layer 48 is preferably hourglass-shaped. The storage layer 48 can alternatively be of any desired shape, for example, rectangular, trapezoidal, oval, or oblong. The shape of the storage layer 48 of the absorbent core 42 will frequently define the general shape of the resulting diaper or absorbent article.

It has been found that a relative capillarity difference between the acquisition aperture 56 and the holding zone 58 is of importance in the overall efficiency and effectiveness of the storage layer 48. While liquid capillarity can be defined in several ways (e.g., pore size, density, basis weight, etc.), the density and basis weight of the structure are the preferred parameters to define liquid capillarity in the storage layer 48 of the present invention. Thus, the acquisition aperture 56 should have both a relatively lower average density and lower average basis weight per unit area than the holding zone 58 to establish the preferred capillarity force gradient between them. Thus, the acquisition aperture 56 comprises an area of zero density and basis weight per unit area.

The holding zone 58 is the relatively higher capillarity (higher density and basis weight per unit area) portion of the storage layer 48. The primary functions of the holding zone 58 are to absorb discharged liquids that are either deposited directly onto the holding zone 58 or transferred to the holding zone 58 via the capillary force gradient established between the liquid handling layer 50 and the holding zone 58, and to prevent liquids acquired by the absorbent core 42 from passing back through the topsheet 38 and onto the skin of the wearer. Preferably, the holding zone 58 consists essentially of the structure of the absorbent member disclosed in the above-referenced U.S. Pat. No. 4,610,678 entitled "High-Density Absorbent Structures", which issued to Paul T. Weisman and Stephen A. Goldman on Sept. 9, 1986, and which is incorporated herein by reference, although other structures may also be used.

The holding zone 58 preferably has a relatively higher density and a higher basis weight per unit area than the acquisition aperture 56. The density and basis weight values of the holding zone 58 include the weight of the particles of absorbent gelling material, such that the density and basis weight values will vary depending upon the amount of particles dispersed throughout the storage layer 48. Thus, the holding zone 58 will generally have a density of from about 0.10 to about 1.0 $g/cm^3$, and more preferably within the range of from about 0.15 to about 0.6 $g/cm^3$, wherein the storage layer 50 contains up to about 60% by weight of particles of absorbent gelling material. The basis weight of such a holding zone 58 can range from about 0.01 to about 0.1 $g/cm^2$, preferably from about 0.015 to about 0.03 $g/cm^2$. The density of the holding zone is calculated from its basis weight and caliper measured on newly unpacked, unfolded, and dissected diapers. The caliper is measured using a standard gauge with a sample under a load of 0.1 psi. The basis weight is measured by die-cutting a certain size sample and weighing this sample on a standard scale, the weight and area of the sample determining the basis weight. (It should be noted that the density and basis weight values include the weight of the particles of absorbent gelling material).

While the holding zone 58 may take on a number of sizes and shapes, it is preferred that the holding zone 58 comprises the remainder of the storage layer 48 (i.e., the portion of the storage layer 48 wherein there is no acquisition aperture 56). While certain portions of the storage layer 48 need not comprise the holding zone 58, in a particularly preferred embodiment of the absorbent core 42 as shown in FIG. 1, the entire storage layer 48 except for the acquisition aperture 56 consists of the holding zone 58. In addition, while the holding zone 58 need not completely laterally surround the acquisition aperture 56 (i.e., it is in liquid communication with at least a portion of the lateral area of the acquisition aperture 56), in preferred embodiments of the present invention, the holding zone 58 laterally surrounds the acquisition aperture 56.

Figure 4:
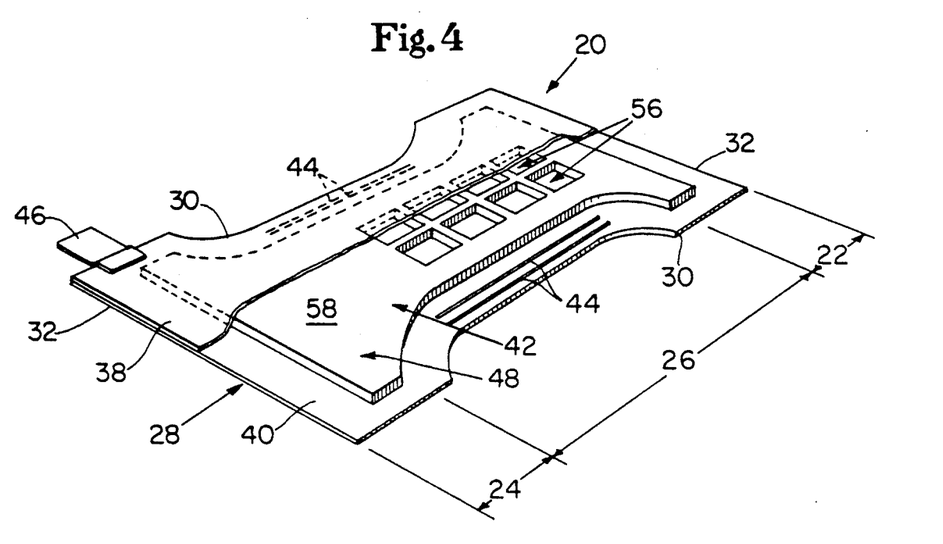
FIG. 4 is a perspective view of a disposable diaper embodiment of the present invention showing multiple acquisition apertures, wherein portions of the topsheet and top tissue layer have been cut-away to more clearly show the underlying absorbent core of the diaper.

The acquisition aperture 56 serves to collect and to distribute to the liquid handling layer 50 reasonably large amounts of discharged liquid. Since such liquids are generally discharged in gushes, the acquisition aperture 56 must be able to quickly acquire and transport liquid from the point of liquid contact to other parts of the absorbent core 42, preferably to the liquid handling layer 50 with a minimum of liquid flow resistance. The acquisition aperture 56 thus has a density of 0.0 $g/cm^3$ and a basis weight of 0.0 $g/cm^2$. As shown in FIG. 4, the acquisition aperture 56 of the present invention preferably comprises one or more acquisition apertures so that a portion of the liquid handling layer 50 is positioned immediately subjacent the topsheet 38. An acquisition aperture 56 also preferably provides improved rates of liquid acquisition because there is reduced interference to liquid flow. Therefore, gushes of liquid will readily and easily pass through the topsheet 38 into the acquisition aperture 56 and onto the liquid handling layer 50 without having an opportunity to flow along the surface of the topsheet. As shown in FIG. 3, the topsheet 38 is preferably secured to the liquid handling layer 50 through the acquisition aperture 56 by attachment means 74 to provide intimate contact between the liquid handling layer 50 and the topsheet 38 so that liquids will not pool or collect on the topsheet 38 but be acquired into the liquid handling layer 50.

The shape, size, and positioning of the acquisition aperture 56 is of importance in determining the effectiveness of the resulting absorbent core 42 in rapidly acquiring discharged liquids. In accordance with the present invention, the acquisition aperture 56 should be placed in a specific positional relationship with respect to the area of typical liquid deposition of the absorbent core 42. While portions of the acquisition aperture 56 may be positioned anywhere in the storage layer 48, the acquisition aperture 56 is preferably positioned generally in the front two-thirds section of the storage layer 48 so that the acquisition aperture 56 is positioned in the area of typical liquid deposition (i.e., the deposition region). Thus, the acquisition aperture 56 is placed in the vicinity of the point of discharge of liquids so as to be capable of quickly acquiring such liquids at their contact zone.

The generally forward positioning of the acquisition aperture 56 can be defined by specifying the percentage of the volume or top surface area of the acquisition aperture 56 which is found forward of particular points along the length of the storage layer 48. While the positioning of the acquisition aperture 56 can be defined with respect to the volume of the acquisition aperture 56 positioned forward of particular points, it has been found that the top surface area of the acquisition aperture 56 is a more desirable definition because the top surface area actually defines the initial area available for liquid acquisition. In addition, since the thickness of the storage layer 48 is preferably uniform and the acquisition aperture 56 has a generally rectangular cross-sectional area, the top surface area definition is equal to a volumetric definition in a preferred embodiment. Thus, the positioning of the acquisition aperture 56 will be referenced throughout the specification as related to its top surface area. (i.e., the percentage of the top surface area of the acquisition aperture positioned in a given area.)

Thus, in accordance with the present invention, at least a portion of the acquisition aperture 56 must be placed in the area of typical liquid deposition, even though remaining portions may be positioned anywhere in the storage layer 48. (It should be understood that if plural acquisition apertures are utilized, at least a portion of one of the acquisition apertures must be positioned in the area of typical liquid deposition.) Thus, at least about 75% of the top surface area of the acquisition aperture 56 is positioned in the front three-fourths, preferably the front two-thirds, section of the storage layer 48. The acquisition aperture 56 is preferably positioned relative to the storage layer 48 such that the top surface area of the acquisition aperture 56 is completely (100%) positioned within the front three-quarters section of the storage layer 48, more preferably the front two-thirds section, and most preferably between the front 10% and 60% of the storage layer 48. The acquisition aperture 56 is also preferably centered about the longitudinal centerline 36 of the diaper 20.

The forward positioning of the acquisition aperture 56 may alternatively be defined by specifying the percentage of the top surface area of the acquisition aperture 56 that is found forward of particular points along the length of the diaper 20 or other absorbent articles. Thus, the acquisition aperture 56 is preferably positioned on the storage layer 48 relative to the backsheet 40 such tht at least a portion, preferably at least about 75%, of the top surface area of the acquisition aperture is in the crotch region 26 of the diaper 20. More preferably, the acquisition aperture 56 is positioned such that its top surface area is completely (100%) positioned in the crotch region 26 and the front region 22 of the diaper 20, most preferably in the crotch region 26.

The acquisition aperture 56 can be of any desired shape consistent with the absorbency requirements of the absorbent core 42 or the diaper 20 including, for example, circular, rectangular, triangular, trapezoidal, oblong, hourglass-shaped, funnel-shaped, dogbone-shaped, fox-shaped, or oval. Preferred shapes of the acquisition aperture 56 are those that increase the perimeter of the lateral interface between the acquisition aperture 56 and the holding zone 58 so that the relative capillarity difference between the zones are fully utilized. In a preferred embodiment as shown in FIGS. 1 and 2, the acquisition aperture 56 will be rectangular-shaped having a top surface area of about 56.5 cm² (8.75 in²) so that the top surface area of the acquisition aperture 56 comprises about 10% of the total surface area (including the top surface area of the acquisition aperture 56) of the storage layer 48 for a medium sized diaper.

In order to maintain a certain minimal absorbency level in the storage layer 48 and reduce the wetback of liquids through the topsheet 38, the top surface area or volume of the holding zone 58 must comprise some minimal amount of the top surface area or volume of the storage layer 48. Thus, it has been found that the acquisition aperture 56 should preferably comprise less than the total surface area and/or volume of the storage layer 48. The top surface area of the acquisition aperture 56 preferably comprises less than about 50% of the total top surface area of the storage layer 48. More preferably, the top surface area of the acquisition aperture 56 comprises less than about 35% of the total top surface area of the storage layer 48, with less than about 20% being especially preferred.

The acquisition aperture 56 may also have a number of different cross-sectional areas and configurations including those wherein the area of portions of the acquisition aperture 56 in planes below the top plane of the storage layer 48 is less than or greater than its top surface area (i.e., the acquisition aperture 56 is smaller or wider below the top surface of the storage layer 48.) For example, the acquisition aperture 56 may have conical, trapezoidal, T-shaped, or rectangular cross-sectional areas. As shown in FIG. 3, the acquisition aperture 56 preferably has a rectangular cross-sectional area.

It should be noted that after processing and handling of the diaper 20 shown in FIG. 1–3, the absorbent core 42 generally will have been compressed such that the portion of the liquid handling layer 50 positioned immediately subjacent the acquisition aperture 56 will expand into the acquisition aperture 56 such that the acquisition aperture 56 appears to be a portion of the liquid handling layer 50 rather than an acquisition aperture 56.

The second component of the absorbent core 42 of the present invention is the liquid handling layer 50. The liquid handling layer 50 serves to quickly collect and transport discharged body liquids into and throughout itself and to other portions of the absorbent core 42. Since such liquids are discharged in gushes, the liquid handling layer 50 must have some gush handling capacity so as to allow liquids to freely and quickly move into the liquid handling layer 50 and the ability to transport liquids either by hydraulic transport or capillary flow from the point of initial contact on the liquid handling layer 50 to other parts of the liquid handling layer 50 and the absorbent core 42. The liquid handling layer 50 also preferably provides a member that contains and quickly acquires subsequent gushes of liquid.

The liquid handling layer 50 must have some gush handling capacity so that the liquid handling layer 50 can rapidly receive practical quantities of liquids and other body exudates. The gush handling capacity of the liquid handling layer 50 is related to the void volume of the structure of the liquid handling layer 50. The liquid handling layer 50 should, therefore, be manufactured of a material that has sufficient void volume in the interstices or capillaries between the material or fibers to contain practical quantities of liquid. Void volume within the liquid handling layer 50 serves as a reservoir or "bucket" for large gushes of liquid with a minimum resistance to flow within the structure so that the liquid handling layer 50 may acquire and transport rapidly voided body liquids.

It has been found that the liquid handling layer 50 should have a percentage void volume greater than about 80%, preferably greater than about 90% (typically between about 93% and 99%), so that there is sufficient void volume to contain in-use quantities of liquids or body exudates. The percentage void volume is calculated by the equation:

$$\text{Percentage void volume} = (1 - V_m/V_s) \times 100\%$$

wherein $V_m$ is the volume of the material determined by dividing the weight of the material or fibers in a given sample by the density of the material or fibers, and wherein $V_s$ is the volume of the sample calculated by multiplying its area times its caliper measured under a load of 0.1 psi. Preferably, the liquid handling layer 50 has a void volume of at least about 5 cm$^3$, more preferably at least about 10 cm$^3$, and most preferably at least about 15 cm$^3$. (In an especially preferred embodiment, the liquid handling layer 50 has a void volume of about 26.4 cm$^3$.)

In order to provide a liquid handling layer 50 that maintains its void volume when placed into a diaper so that the liquid handling layer 50 is especially effective in acquiring initial and subsequent gushes of liquid, the liquid handling layer 50 should be resilient. The liquid handling layer 50 should be resilient so that it must, without the application of external forces, return to essentially its original size and shape after the forces which are applied to it are removed. Preferably, the material used in manufacturing the liquid handling layer 50 possesses such resiliency that it will recover at least about 80% of its original volume after it is compressed to about 20% of its original volume when the compressing forces are removed. Most preferably, the material will recover at least about 90% of the original volume after it is compressed to about 50% of its original volume when the compressing forces are removed.

Because the absorbent core 42 needs to be able to acquire subsequent gushes of liquid deposited onto it, the liquid handling layer 50 should also be essentially unaffected by the presence of liquids such as urine; that is to say, the liquid handling layer 50 should possess a high degree of wet resiliency. The liquid handling layer 50 should retain sufficient inherent resiliency, even when wet, to impart to the liquid handling layer 50 sufficient resiliency to resist close packing of the absorbent material or fibers and retention of the characteristics of the "springy" three dimensional structure so that the liquid handling layer 50 will maintain its void volume and ability to contain gushes of liquid subsequently deposited onto the liquid handling layer 50. Certain materials and fibers, such as rayon or cellulose fibers, have a high degree of resiliency in the dry state, but are essentially non-resilient when wetted. Such materials and fibers are, in general, not useful in the present invention as a liquid handling layer 50. The term "moisture insensitive" is used herein to describe materials and fibers whose resiliency is relatively unaffected by the presence of moisture (wet resilient).

The liquid handling layer 50 also must allow the liquids to quickly penetrate into itself and transport those liquids to other portions of the liquid handling layer 50 and eventually to the holding zone 58 of the storage layer 48. The liquid handling layer 50 should thus, it is believed, have low resistance to flow of liquids into and throughout the structure, a high permeability to allow liquids to be hydraulically transported into and throughout the liquid handling layer 50, and a low capillarity to allow capillary flow within the structure and enhance liquid transfer from the liquid handling layer 50 to the storage layer 48. Thus, the liquid handling layer 50 should preferably have a relatively lower capillarity (e.g., larger pore size or lower average density and/or basis weight per unit area) than the holding zone 58 so that liquids are transferred to the holding zone 58 wherein the liquids are contained and stored.

Preferably, the liquid handling layer 50 comprises a mass or batt of synthetic fibers. While the liquid handling layer 50 can comprise other materials, such as synthetic foam materials or resilient polmeric foams, the use of such materials is less preferred than the use of a fibrous batt.

Synthetic fibers useful in the present invention include those made of cellulose acetate, polyvinyl fluoride, polyvinylidene chloride, acrylics (such as Orlon), polyvinyl acetate, non-soluble polyvinyl alcohol, polyethylene, polypropylene, polyamides (such as nylon), polyesters, bicomponent fibers, tricomponent fibers, mixtures thereof and the like. Especially preferred fibers are polyester fibers. Preferred fibers have a denier of from about 3 denier per filament to about 25 denier per filament, most preferably from about 5 denier per filament to about 16 denier per filament.

The batt of fibers is preferably formed of hydrophobic fibers of a synthetic material because these types of materials exhibit an inherent dry and wet resilience. Other materials may also be used as long as the fibers exhibit dry and wet resilience. For example, fibers that are bonded together at their point of intersection usually exhibit the necessary wet and dry resilience. As indicated herein, the resiliency of the liquid handling layer 50 can frequently be enhanced if the fibers are bonded together at their points of contact. Thus, the material will have a higher resistance to compression such that the void volume of the material will be maintained even under load. Thermal bonding, resin bonding, heat-through bonding, powder bonding, chemical bonding or adhesive bonding can be used to bond the synthetic fibers one to another.

Since the preferred fibers are hydrophobic and will not absorb liquids into their interiors, the surfaces of the fibers are also hydrophobic. Therefore, in order for the interstices of the batt of fibers to more easily acquire sufficient quantities of liquids into the structure of the liquid handling layer 50, the surfaces of the fibers can be rendered hydrophilic. More generally, the liquid handling layer 50 can comprise a material having interstices or capillaries which are wetted by the liquids in question. Urine and other body liquids are primary liquid aqueous solutions and suspensions; surfaces which are wetted by these liquids can be broadly described as hydrophilic. As used in this specification, the term "hydrophilic" describes surfaces which are wetted by the liquid in question. The state of the art respecting wetting of materials allows a definition of hydrophilicity (and wetting) in terms of contact angles and the surface tension of the liquids and solids involved. This is discussed in detail in The American Chemical Society Publication entitled, Contact Angle, Wettability, and Adhesion, edited by Robert F. Gould and copyrighted in 1964, which publication is incorporated herein by reference. A surface is said to be wetted by a liquid either when the contact angle between the liquid and the surface is less than 90° or when the liquid will tend to spread spontaneously across the surface; both conditions normally coexisting.

The materials used in the liquid handling layer 50 can achieve hydrophilicity by any convenient means. For example, the material itself can be extrinsicly hydrophilic, although as discussed herein, this circumstance is relatively rare for materials useful in the liquid handling layer 50. The surfaces of the liquid handling layer 50 can be rendered hydrophilic by treatment with a surfactant, such as a non-ionic or anionic surfactant, as by spraying the material with a surfactant or by dipping the material into the surfactant. By treating the surfaces of the fibers with a surfactant, only the surfaces of the fibers exhibit hydrophilic characteristics while the fiber itself remains hydrophobic. Suitable surfactants include non-ionic surfactants such as Brij 76 manufactured by ICI Americas, Inc. of Wilmington, Del. and the various materials sold under the Pegosperse trademark by Glyco Chemical, Inc. of Greenwich, Conn. Anionic surfactants can be also used. Surfactants are applied to the fibers at a level of from about 0.2 to about 1 gram per square meter of material.

In order to maintain a high void volume and a high level of liquid transport, it is believed that the batt of synthetic fibers of the liquid handling layer 50 should have a caliper, measured under a load of 0.1 psi, of greater than about 0.25 mm (0.01 inches), preferably greater than about 0.38 mm (0.015 inches), more preferably greater than about 0.5 mm (0.02 inches), and most preferably greater than about 0.63 mm (0.025 inches). The basis weight of the batt of fibers is preferably between about 15 to about 75 g/yd$^2$, most preferably about 20 to about 30 g/yd$^2$.

A most preferred execution of the liquid handling layer 50 comprises a batt of polyester fibers such as Kodel type 435 polyester fibers that are powder bonded into an open structure. The fibers have a denier of about 5.5 denier per filament, a basis weight of about 30 grams per square yard, a caliper under load at 0.1 psi of about 0.68 mm (0.027 inches), and a percentage void volume of about 96%. Such a batt is manufactured by the Eastman Chemical Company of Kingsport, Tenn.. Alternatively preferred examples include batts of polyester fibers that are chemically bonded, have a denier of about 6 denier per fiber and a basis weight of 30 grams per square yard; or that are powder bonded, have a denier of about 15 denier per fiber, and basis weight of 75 grams per square yard. Other examples of suitable batts of fibers useful in the present invention are found in U.S. Pat. No. 4,738,676 entitled "Pantiliner" which issued to Thomas W. Osborn, III, on Apr. 19, 1988 which is incorporated herein by reference.

Synthetic foams useful as the liquid handling layer 50 include polyester foam materials (such as those described in U.S. Pat. No. 4,110,276 issued to DeMarais on Aug. 29, 1978, and incorporated herein by reference), polyurethane foams, styrene-butadiene foams, resilient polymeric foams, and cellulose sponge material. Synthetic foams should be soft, flexible and open-celled. Its interior surfaces are preferably hydrophilic. Incorporation of surfactant during foam manufacture or addition of surfactants to the performed foam are two suitable methods of insuring that the interior surfaces are hydrophilic.

The liquid handling layer 50 of the absorbent core 42 need not be the same size as the storage layer 48 of the absorbent core 42 and preferably has a top surface area which is substantially smaller than the top surface area of the storage layer 48 (including the top surface area of the acquisition aperture 56). Generally, the top surface area of the liquid handling layer 50 will be not less than the surface area of the acquisition aperture 56 of the storage layer 48. Most preferably, the top surface area of the liquid handling layer 50 will be from about 0.1 to about 1.0, more preferably from about 0.2 to about 0.75, and most preferably from about 0.25 to about 0.5, times the total top surface area of the storage layer 48.

The liquid handling layer 50 of the absorbent core 42 should be placed in a specific positional relationship with respect to the acquisition aperture 56. More particularly, the liquid handling layer 50 of the absorbent core 42 should be positioned at least subjacent the acquisition aperture 56 of the storage layer 48 so that the liquid handling layer 50 is most effectively located to quickly acquire and distribute discharged body liquid deposited onto the absorbent core 42. Thus, the liquid handling layer 50 is placed generally in the vicinity of the point of discharge of body liquids.

The liquid handling layer 50 of the absorbent core 42 can be of any desired shape consistent with comfortable fit including, for example, circular, rectangular, trapezoidal, oblong, hourglass-shaped, dogbone-shaped, or oval. The liquid handling layer 50 need not be physically separated from the storage layer 48 and can simply form a zone in a continuous web of material. More preferably, however, the liquid handling layer 50 will comprise a separate web which can be used as an insert positioned subjacent the acquisition aperture 56 of the storage layer 48. In preferred embodiments, the liquid handling layer 50 will be rectangular.

Referring again to FIG. 3 which illustrates a preferred embodiment of the present invention, a top tissue layer 66 is interposed between the topsheet 38 and the storage layer 48 of the absorbent core 42. Any material which increases the tensile strength of the storage layer 48 can be used as the top tissue layer 66. Preferably, the top tissue layer 66 comprises a sheet or sheets of tissue paper closely associated with the inner surface of the topsheet 38. Tissue papers used in commonly available facial tissue products, such as that marketed under the registered trademark PUFFS by the Procter & Gamble Company of Cincinnati, Ohio can be used. Especially preferred are tissue papers manufactured by either of the processes described in U.S. Pat. No. 3,301,746 issued to Sanford and Assarsson on Jan. 31, 1967 and U.S. Pat. No. 3,994,771 issued to Morgan and Rich on Nov. 30, 1976. Both of these patents are incorporated herein by reference. The top tissue layer 66 preferably does not overlie the acquisition aperture 56 of the storage layer 48 so that liquids may readily penetrate the topsheet 38 into the liquid handling layer 50 through the acquisition aperture 56 of the storage layer 48. Thus, if a single sheet of tissue paper is utilized as the top tissue layer 66, the tissue paper should have an aperture formed in the tissue that coincides with the acquisition aperture 56 of the storage layer 48. Alternatively, and most preferably, two separate pieces of tissue paper, first tissue layer 68 and second tissue layer 70, are positioned over the storage layer 48 so that the tissue layers are laterally spaced from each other by at least a dimension equal in width to the width of the acquisition aperture 56 so as to form a tissue acquisition aperture 72.

As shown in FIG. 3, the topsheet 38 is preferably joined to the liquid handling layer 50 through the acquisition aperture 56 of the storage layer 48 by attachment means 74 such as those well known in the art. For example, the topsheet 38 may be joined to the liquid handling layer 50 by a uniform continuous layer of adhesive, a patterned layer of adhesive, an array of separate lines or spots of adhesive, or by ultrasonically welding or bonding such as is known in the art. An adhesive which has been found to be satisfactory for use as the attachment means 74 is preferably a hot-melt adhesive such as manufactured by Eastman Chemical Products Company of Kingsport, Tenn. and marketed under the tradename of Eastobond A-3 or by Century Adhesives, Inc. of Columbus, Ohio and marketed under the tradename Century 5227. The attachment means 74 preferably comprises an open patterned network of filaments of adhesive as is shown in U.S. Pat. No. 4,573,986 entitled "Disposable Waste-Containment Garment", which issued to James A. Minetola and David R. Tucker on Mar. 4, 1986, and which is incorporated herein by reference.

An absorbent core layer similar to the storage layer 48 can be formed by air-laying a dry mixture of hydrophilic fibers and particles of absorbent gelling material and densifying the resultant web. Such a procedure is described more fully in the hereinbefore referenced U.S. Pat. No. 4,610,678; incorporated by reference herein. The liquid handling layer 50 may be separately formed and inserted between the storage layer 48 and the backsheet 40 or may be formed with the storage layer 48 in one process.

Without wishing to be bound by theory, it is believed that the absorbent core 42 described herein achieves a lower level of leakage of liquids in the following manner. Liquids, such as urine and other body exudates, that are deposited onto the topsheet 38 pass through the topsheet 38 to the acquisition aperture 56. Since the topsheet 38 is joined to the liquid handling layer 50 through the acquisition aperture 56, there is lower resistance to the flow of liquid through the storage layer 48 to the liquid handling layer 50. Because of the relatively high amount of void volume within the liquid handling layer 50, the liquid handling layer acts as a reservoir to acquire the liquids within its structure. Due to the ability of the liquid handling layer 50 to transport liquid, the liquid is distributed to portions of the liquid handling layer 50 remote from the acquisition aperture 56. Due to the capillarity difference between the liquid handling layer 50 and the storage layer 48 (the holding zone 58), liquids are in essence "pumped" or drawn out of the liquid handling layer 50 and into the storage layer 48 wherein the absorbent gelling material and the hydrophillic fibers contain the liquid. The liquid handling layer 50 is thus drained of the initial gush of liquid, and because it is moisture insensitive, it has sufficient void volume to contain subsequent gushes of liquid, wherein the process described cycles again.

In use, the diaper 20 is applied to a wearer, by positioning the back region 24 under the wearer's back, and drawing the remainder of the diaper 20 between the wearer's legs so that the front region 22 is positioned across the front of the wearer. The ends of the tape-tab fasteners 46 are then secured preferably to outwardly facing areas of the diaper 20. In use, disposable diapers or other absorbent articles having such absorbent cores 42 as described herein tend to more quickly acquire liquid into the absorbent core and remain dry or dryer due to the preferential capillarity of the absorbent core 42. Thus, such an absorbent core 42 helps to alleviate leakage around the edges of such absorbent articles.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article comprising:
    a liquid pervious topsheet;
    a liquid impervious backsheet joined with said topsheet; and
    an absorbent core positioned between said backsheet and said topsheet, said absorbent core comprising:
        a storage layer comprising a web of hydrophilic fibrous material and discrete particles of absorbent gelling material, and having an acquisition aperture; and
        a liquid handling layer positioned subjacent at least said acquisition aperture of said storage layer so that said liquid handling layer is positioned between said storage layer and said backsheet of said absorbent article, said liquid handling layer comprising a resilient material having gush handling capacity to receive quantities of body exudates, said liquid handling layer being moisture insensitive and having a percentage void volume greater than about 80%.

2. The absorbent article of claim 1 wherein said liquid handling layer has a relatively lower capillarity than said web of said storage layer.

3. The absorbent article of claim 2 wherein said liquid handling layer comprises a batt of synthetic fibers.

4. The absorbent article of claim 3 wherein said batt of synthetic fibers is bonded into an open structure with a caliper of greater than about 0.25mm.

5. The absorbent article of claim 4 wherein said batt of synthetic fibers has a void volume of at least about 5 $cm^3$.

6. The absorbent article of claim 1 wherein said storage layer has a density of from about 0.1 to about 1.0 $g/cm^3$.

7. The absorbent article of claim 6 wherein said storage layer has a fiber to particulate weight ratio of from about 40:60 to about 98:2.

8. The absorbent article of claim 7 wherein said hydrophilic fibers are wood pulp fibers.

9. The absorbent article of claim 1 wherein said liquid handling layer comprises a synthetic foam.

10. The absorbent article of claim 1 wherein said acquisition aperture comprises multiple acquisition apertures.

11. The absorbent article of claim 1 wherein said acquisition aperture is rectangular shaped.

12. The absorbent article of claim 1 wherein said acquisition aperture has a top surface area less than about 50% of the total top surface area of said storage layer.

13. The absorbent article of claim 1 wherein said acquisition aperture is positioned so that at least about 75% of the top surface area of said acquisition aperture is positioned in the front two-thirds section of said storage layer.

14. A disposable absorbent article comprising:
    a liquid pervious topsheet;
    a liquid impervious backsheet joined with said topsheet; and
    an absorbent core positioned between said backsheet and said topsheet, said absorbent core comprising:
        a storage layer comprising a web of hydrophilic fibrous material and discrete particles of absorbent gelling material in a fiber to particulate weight ratio of from about 40:60 to about 98:2, said web having a density of from about 0.1 $g/cm^3$ to about 1 $g/cm^3$, said storage layer having an acquisition aperture positioned so that at least about 75% of the top surface area of said acquisition aperture is positioned in the front two-thirds section of said storage layer, said acquisition aperture having a top surface area less than about 35% of the total top surface area of said storage layer; and a liquid handling layer positioned subjacent at least said acquisition aperture of said storage layer, said liquid handling layer comprising a resilient batt of synthetic fibers having interstices to provide sufficient gush handling capacity to receive quantities of body exudates, said liquid handling layer being moisture insensitive and having a percentage void volume greater than about 90%.

15. The absorbent article of claim 14 wherein said acquisition aperture is completely positioned within the front two-thirds section of said storage layer.

16. The absorbent article of claim 15 wherein said liquid handling layer comprises polyester fibers.

17. The absorbent article of claim 16 wherein said liquid handling layer has a void volume of at least about 5 cm$^3$.

18. The absorbent article of claim 17 wherein said liquid handling layer has a top surface area from about 0.1 to about 1.0 times that of said storage layer.

19. The absorbent article of claim 18 wherein said storage layer has a density of from about 0.15 g/cm$^3$ to about 0.6 g/cm$^3$.

20. The absorbent article of claim 19 wherein said acquisition aperture is rectangular shaped.

21. An absorbent core suitable for use in an absorbent article, said absorbent core comprising:

a storage layer comprising a web of hydrophilic fibrous material and discrete particles of absorbent gelling material, and having an acquisition aperture positioned so that at least about 75% of the top surface area of said acquisition aperture is positioned in the front two-thirds section of said storage layer; and a liquid handling layer positioned subjacent at least said acquisition aperture of said storage layer, said liquid handling layer comprising a resilient material having gush handling capacity to receive quantities of body exudates, said liquid handling layer being moisture insensitive and having a percentage void volume greater than about 80%.

22. The absorbent core of claim 21 wherein said liquid handling layer comprises a batt of synthetic fibers.

23. The absorbent core claim 22 wherein said liquid handling layer has a caliper greater than about 0.25 mm and a void volume of at least about 5 cm$^3$.

24. The absorbent core of claim 23 wherein said storage layer has a density of from about 0.1 g/cm$^3$ to about 1.0 g/cm$^3$, and a fiber to particulate weight ratio of from about 40:60 to about 98:2.

25. The absorbent core of claim 24 wherein said storage layer is hourglass-shaped.

* * * * *